(12) United States Patent
Bobrove et al.

(10) Patent No.: US 6,395,757 B1
(45) Date of Patent: *May 28, 2002

(54) METHOD FOR TREATING HOT FLASHES IN HUMANS

(76) Inventors: Arthur M. Bobrove, 1539 Walnut Dr., Palo Alto, CA (US) 94030; Jeffrey D. Urman, 1880 Hamilton Ave., Palo Alto, CA (US) 94303

( * ) Notice: Subject to any disclaimer, the term of this patent is extended or adjusted under 35 U.S.C. 154(b) by 0 days.

This patent is subject to a terminal disclaimer.

(21) Appl. No.: 09/360,074

(22) Filed: Jul. 23, 1999

Related U.S. Application Data

(63) Continuation of application No. 09/184,512, filed on Nov. 2, 1998, now Pat. No. 5,962,505.
(60) Provisional application No. 60/098,629, filed on Aug. 31, 1998.

(51) Int. Cl.$^7$ ........................ A61K 31/445; A61K 31/40
(52) U.S. Cl. ........................ 514/327; 514/424
(58) Field of Search ........................ 514/327, 424

(56) References Cited

U.S. PATENT DOCUMENTS

| | | |
|---|---|---|
| 2,956,062 A | 10/1960 | Lunsford |
| 3,943,242 A | 3/1976 | Fogel et al. |
| 4,096,254 A | 6/1978 | Benson et al. |
| 5,008,111 A | 4/1991 | Bodor |
| 5,155,045 A | 10/1992 | Cutler et al. |
| 5,223,528 A | 6/1993 | Hammer et al. |
| 5,258,388 A | 11/1993 | Hammer et al. |
| 5,462,950 A | 10/1995 | Fontana |
| 5,512,555 A | 4/1996 | Waldstreicher |
| 5,525,347 A | 6/1996 | Kellner et al. |
| 5,637,601 A | 6/1997 | Hammer et al. |
| 5,730,964 A | 3/1998 | Waldstreicher |
| 5,744,463 A | 4/1998 | Bair |
| 5,962,505 A | * 10/1999 | Bobrove et al. ............ 514/424 |

OTHER PUBLICATIONS

Abell and Morgan, "The treatment of idiopathic hyperhidrosis by glycopyrronium bromide and tap water iontophoresis" *British Journal of Dermatology* (1974) 91:87–91.

Atkin and Brown, (1996) "Treatment of Diabetic Gustatory Sweating with Topical Glycopyrrolate Cream" *Diabetic Medicine* 13:493–494.

Hays, (1978) "The Frey Syndrome: A Review and Double Blind Evaluation of the Topical Use of a New Anticholinergic Agent" *The Laryngoscope* 88:1796–1824.

Hays et al., (1982) "The Frey Syndrome: A Simple Effective Treatment" *Otolaryngol Head Neck Surg* 90:419–425.

Goldberg et al., (1994) "Transdermal Clonidine for Ameliorating Tamoxifen–induced Hot Flashes" *J. Clin Onc.* 12:155–158.

Loprinzi et al., (1994) "Megestrol Acetate for the Prevention of Hot Flashes" *N. Engl. J. Med.* 331:347–351.

May and McGuirt, (1989) "Frey's Syndrome: Treatment with Topical Glycopyrrolate" *Head & Neck* 11:85–89.

Shaw et al., (1997) "A Randomised Controlled Trial of Topical Glycopyrrolate, the First Specific Treatment for Diabetic Gustatory Sweating" *Diabetologia* 40:299–301.

Stegehuis and Ellis, (1989) "Treatment of Frey's Syndrome (Gustatory Sweating) with Topical Glycopyrrolate: Case Report" *NZ Med J.* 103(875):479.

Merck Index, Ninth Edition, Merck & Co., Rahway, NJ, p. 583, #4337 (1976).

* cited by examiner

*Primary Examiner*—Russell Travers
*Assistant Examiner*—Shengjun Wang
(74) *Attorney, Agent, or Firm*—Burns, Doane, Swecker & Mathis LLP

(57) ABSTRACT

This invention is directed to methods for treating hot flashes as a consequence of declining levels of estrogen or androgen in humans. Specifically, the methods of this invention involve the topical administration of a glycopyrrolate analog of Formula (I) to humans.

18 Claims, No Drawings

METHOD FOR TREATING HOT FLASHES IN HUMANS

CROSS-REFERENCE TO RELATED APPLICATIONS

This application claims priority to provisional U.S. Patent Application No. 60/098,629 filed Aug. 31, 1998, and a continuation of U.S. patent application Ser. No. 09/184,512 filed Nov. 2, 1998, and now U.S. Pat. No. 5,962,505, which are incorporated herein in their entirety.

BACKGROUND OF THE INVENTION

1. Field of the Invention

This invention is directed to methods for treating hot flashes as a consequence of declining estrogen levels or androgen levels in humans. Specifically, the methods of this invention involve the topical administration of a therapeutically effective amount of a glycopyrrolate analog to a human suffering from hot flashes.

2. References

The following publications, patent applications and patents are cited in this application as superscript numbers:

1. Loprinzi et al., "Megestrol acetate for the prevention of hot flashes" *N. Engl. J. Med.* 331:347–351 (1994)
2. Goldberg et al., "Transdermal clonidine for ameliorating tamoxifen-induced hot flashes" *J. Clin. Onc.* 12:155–158 (1994)
3. Hays et al., "The Frey syndrome: a simple, effective treatment" *Otolaryngol Head Neck Surg.* 90:419–425 (1982)
4. Atkin et al., "Treatment of diabetic gustatory sweating with topical glycopyrrolate cream" *Diabetic Medicine* 13:493–494 (1996)
5. Shaw et al., "A randomized controlled trial of topical glycopyrrolate, the first specific treatment for diabetic gustatory sweating" *Diabetologia* 40:299–301 (1997)
6. May et al., "Frey's Syndrome: Treatment with topical glycopyrrolate" *Head & Neck* (January/February 1989) p.85–89
7. Col. Leonard L. Hays, "The Frey syndrome: A review and double blind evaluation of the topical use of a new anticholinergic agent" *The Laryngoscope* 88:1976 (1978)
8. *Remington's Pharmaceutical Sciences,* Mace Publishing Company Philadelphia Pa. 17$^{th}$ ed. (1985)
9. U.S. Pat. No. 5,525,347, Kellner et al.
10. U.S. Pat. No. 2,956,062, Lunsford et al.

All of the above publications, patent applications and patents are herein incorporated by reference in their entirety to the same extent as if each individual publication, patent application or patent was specifically and individually indicated to be incorporated by reference in its entirety.

3. State of the Art

Hot flashes or flushing occur commonly in menopausal women. This is characterized by a sudden onset of warmth in the face and neck and often progressing to the chest. Such an episode generally lasts several minutes and is evidenced by a visible flushing of the skin. Often such episodes are accompanied by sweating, dizziness, nausea, palpitations and diaphoresis. Such symptoms can disrupt sleep and interfere with the quality of life. Although the cause of hot flashes is not completely understood, they are thought to be a disorder of thermoregulation within the hypothalamus that is a consequence of declining estrogen levels. Thus it is not surprising that hot flashes also occur in a high percentage of women taking the anti-estrogen drug tamoxifen.

Men may also have hot flashes following androgen-deprivation therapy (from bilateral orchiectomy or treatment with a gonadotrophin-releasing-hormone agonist) for metastatic prostate cancer.

Although estrogen replacement therapy is the most direct and effective treatment for hot flashes in women, there are women in whom such therapy is contraindicated, i.e. women with breast cancer or a strong family history of breast cancer, a history of clotting, severe migraine, or who are averse to taking the drug.

In these women, there are alternative medications to prevent or treat the serious consequences of menopause, such as osteoporosis and raised serum lipid levels. Included in this category are the selective estrogen-receptor modulators (SERMs), such as raloxifene, which selectively bind to and activate the estrogen receptors of some tissues such as bone, and block the receptors of others, i.e. breast and uterus. In so doing, they lack the negative impact that prolonged estrogen therapy may have on these organs. However, in contrast to estrogen, SERMs do not prevent hot flashes.

Other than estrogen-replacement therapy, there are no effective means to alleviate hot flashes. Low dose oral megestrol acetate, a progestational agent, was shown to reduce the frequency of hot flashes in both men and women in a short term study[1]. However, chronic adrenal insufficiency can be a side effect of low dose megestrol acetate when taken long term. Transdermal clonidine, a centrally active α-agonist, had only a moderate effect on the frequency and severity of hot flashes in tamoxifen-treated women[2]. Accordingly, there is a need for a method of treating hot flashes.

Topical glycopyrrolate has been used previously to treat gustatory sweating associated with diabetic autonomic neuropathy[4,5]. In this disorder, sweating that often is profuse, begins soon after the patient ingests food, starting on the forehead and then involving the face, scalp and neck. A solution of glycopyrrolate was applied to the face of the patient which prevented the gustatory sweating.

Similarly, glycopyrrolate has also been used previously to treat gustatory sweating associated with Frey's syndrome which may develop after parotidectomy[3,6,7]. Frey's syndrome is believed to result from the aberrant reinnervation of the sweat glands of the face by the severed parotid parasympthetic nerve fibers.

In both diabetic gustatory sweating and Frey's syndrome, the profuse facial sweating is induced by the specific stimulus of eating. Moreover, the sweating in each is a consequence of a distinct neuropathological process. In contrast, the hot flashes of menopause occur spontaneously without a specific stimulus and are the consequence of a normal or physiological process, the natural decline in circulating levels of estrogen.

This invention is directed in part to the discovery that the transdermal application of a glycopyrrolate analog to a human overcomes many of the prior problems in treating hot flashes and the perspiration associated therewith. Additionally, it provides advantages heretofore not achieved by conventional treatments for the hot flashes associated with low levels of estrogen and/or androgen. For example, the glycopyrrolate analog to be applied does not have the side effects associated with estrogen replacement therapy. Secondly, the glycopyrrolate analogs can be applied to both males and females.

SUMMARY OF THE INVENTION

This invention is directed to methods for treating hot flashes by the topical application of a therapeutically effective amount of a glycopyrrolate analog of Formula (I):

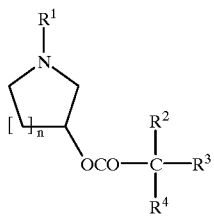

(I)

wherein:

n is 1 or 2;

R¹ is alkyl or phenylalkyl;

R² is phenyl which is optionally substituted with alkyl, halo, alkoxy, hydroxy, or acyloxy, or -(alkylene)-$CO_2R^5$ wherein R⁵ is alkyl, alkenyl, cycloalkyl, or cycloalkenyl;

R³ is cycloalkyl, cycloalkenyl, heteroaryl, phenyl which is optionally substituted with alkyl, halo, alkoxy, hydroxy, or acyloxy;

R⁴ is hydrogen, hydroxy, or acyl; or an acid addition, alkyl, or benzyl quaternary ammonium salt, individual isomer or a mixture of isomers thereof to a human such that the hot flashes are substantially reduced.

Preferably, the glycopyrrolate analog is a compound of Formula (II):

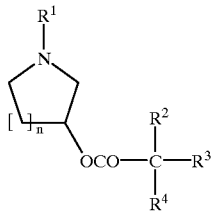

(II)

wherein:

n is 1 or 2;

R¹ is alkyl;

R² is phenyl which is optionally substituted with alkyl, halo, alkoxy, hydroxy, or acyloxy;

R³ is cycloalkyl;

R⁴ is hydroxy; or an acid addition, alkyl, or benzyl quaternary ammonium salt, individual isomer or a mixture of isomers thereof to a human such that the hot flashes are substantially reduced.

Even more preferably, the glycopyrrolate analog of Formula (II) is a compound where:

n is 1;

R¹ is ethyl, propyl, or butyl;

R² is phenyl which is optionally substituted with methyl, ethyl, propyl, fluoro, chloro, methoxy, ethoxy, hydroxy, or acetyloxy;

R³ is pentyl or hexyl;

R⁴ is hydroxy; or an acid addition, alkyl, or benzyl quaternary ammonium salt, individual isomer or a mixture of isomers thereof to a human such that the hot flashes are substantially reduced.

This invention is also directed to a method for alleviating the hot flashes in a human, which method comprises the steps of identifying a human susceptible to hot flashes; and administering to said human a therapeutically effective amount of a glycopyrrolate analog of Formula (I):

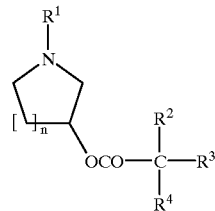

(I)

wherein:

n is 1 or 2;

R¹ is alkyl or phenylalkyl;

R² is phenyl which is optionally substituted with alkyl, halo, alkoxy, hydroxy, or acyloxy, or —(alkylene)—$CO_2R^5$ wherein R⁵ is alkyl, alkenyl, cycloalkyl, or cycloalkenyl;

R³ is cycloalkyl, cycloalkenyl, heteroaryl, phenyl which is optionally substituted with alkyl, halo, alkoxy, hydroxy, or acyloxy;

R⁴ is hydrogen, hydroxy, or acyl; or an acid addition, alkyl, or benzyl quaternary ammonium salt, individual isomer or a mixture of isomers thereof to a human such that the hot flashes are substantially reduced.

This invention is also directed to a method for alleviating hot flashes in a human, which method comprises the steps of identifying a human susceptible to hot flashes; and administering to said human a therapeutically effective amount of a pharmaceutical composition comprising a pharmaceutically acceptable excipient and a glycopyrrolate analog of Formula (I):

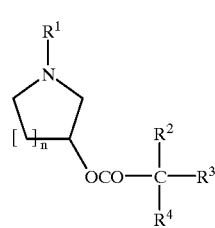

(I)

wherein:

n is 1 or 2;

R¹ is alkyl or phenylalkyl;

R² is phenyl which is optionally substituted with alkyl, halo, alkoxy, hydroxy, or acyloxy, or —(alkylene)—$CO_2R^5$ wherein R⁵ is alkyl, alkenyl, cycloalkyl, or cycloalkenyl;

R³ is cycloalkyl, cycloalkenyl, heteroaryl, phenyl which is optionally substituted with alkyl, halo, alkoxy, hydroxy, or acyloxy;

R⁴ is hydrogen, hydroxy, or acyl; or an acid addition, alkyl, or benzyl quaternary ammonium salt, individual isomer or a mixture of isomers thereof to a human such that the hot flashes are substantially reduced.

DETAILED DESCRIPTION OF THE INVENTION

Definitions

As used herein, the following terms have the following meanings:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Acyloxy" means a radical —OC(O)R where R is hydrogen, alkyl, alkenyl, cycloalkyl, or haloalkyl, e.g., acetoxy, 3,3,3-trifluoroacetoxy and the like.

"Cycloalkyl" means a saturated monovalent cyclic hydrocarbon radical of three to six ring carbons, e.g., cyclopropyl, cyclopentyl, cyclohexyl, and the like.

"Cycloalkenyl" means a monovalent cyclic hydrocarbon radical of three to six ring carbons containing at least a double bond, e.g., cyclopropenyl, cyclopentenyl, cyclohexenyl, and the like.

"Halo" means fluoro, chloro, bromo, or iodo.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroaryl" means a monovalent monocyclic or bicyclic aromatic radical of 5 to 10 ring atoms containing one, two, or three ring heteroatoms selected from N, O, or S, the remaining ring atoms being C. The heteroaryl ring is optionally substituted independently with one or more substituents, preferably one or two substituents, selected from alkyl, haloalkyl, halo, nitro, cyano, —OR (where R is hydrogen, alkyl, or haloalkyl) or amino. More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl and benzodiazepin-2-one-5-yl, and the derivatives thereof.

"Alkoxy" means a radical —OR where R is an alkyl as defined above e.g., methoxy, ethoxy, and the like.

"Acyl" means a radical —C(O)R where R is hydrogen or alkyl as defined above e.g., formyl, —$COCH_3$, and the like.

"Optional" or "optionally" means that the subsequently described event or circumstance may but need not occur, and that the description includes instances where the event or circumstance occurs and instances in which it does not. For example, "phenyl optionally substituted with an alkyl group" means that the alkyl may but need not be present, and the description includes situations where the phenyl group is substituted with an alkyl group and situations where the phenyl group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention possess at least one asymmetric center; and therefore are produced as individual (R)- or (S)-stereoisomers or as mixtures thereof. For example, the carbon to which the —$OCOR^2R^3R^4$ group is attached is an asymmetric center and therefore the compound of Formulae (I) and (II) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

"Phenylalkyl" means a radical —$R^aR^b$ where $R^a$ is an alkylene group and $R^b$ is phenyl group as defined above e.g., benzyl, phenylethyl, and the like.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Acid addition quaternary ammonium salt" is a salt formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like.

Quaternary ammonium salts such as alkyl or benzyl salts are salts formed with organic bases such as methyl iodide, methyl bromide, methyl iodide, methyl sulfonate, ethyl iodide, ethyl bromide, ethyl iodide, ethyl sulfonate, propyl iodide, propyl bromide, propyl iodide, propyl sulfonate, benzyl iodide, benzyl bromide, benzyl iodide, benzyl sulfonate, and the like.

The term "therapeutically effective amount" means that amount of a drug or pharmaceutical agent that will elicit the biological or medical response of a tissue, system, animal or human that is being sought by a researcher, veterinarian, medical doctor or their clinician. In particular, with regard to treating the disorders of hot flashes and perspiration associated therewith, the "therapeutically effective amount" is intended to mean that amount of the glycopyrrolate compound that will prevent or alleviate the hot flashes. Hot flashes are a condition commonly known and understood by the average consumer who lacks any medical skill.

GENERAL SYNTHETIC SECTION

Compounds of this invention can be made by the methods described below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Compounds of Formula (I) are either well known in the art or they can be prepared by methods well known in the art. For example, compounds of Formula (I) where n is 1, $R^1$ is alkyl or phenylalkyl, $R^2$ is phenyl, $R^3$ is cycloalkyl, and $R^4$ is hydrogen or hydroxy can be prepared by methods described in U.S. Pat. No. 2,956,062. Compounds of Formula (I) where n is 1 or 2, $R^1$ is alkyl or phenylalkyl, $R^2$ is —(alkylene)—$CO_2R^5$ where $R^5$ is as defined in the Summary of the Invention, $R^3$ is cycloalkyl, cycloalkenyl, heteroaryl, or phenyl optionally substituted with alkyl, halo, alkoxy, hydroxy, or acyloxy, and $R^4$ is hydrogen can be prepared by the methods described in U.S. Pat. No. 5,223,528.

Utility

The glycopyrrolate analogs of the present invention when applied to the skin of humans suffering from hot flashes as a consequence of reduced levels of estrogen and androgen, reduce or eliminate the incidence of unwanted hot flashes and perspiration.

Formulation and Administration

The glycopyrrolate analog of Formula (I) is effective over a wide dosage range and is generally administered in a therapeutically effective amount. It will be understood, however, that the amount of the compound actually administered may be determined by a physician in light of the relevant circumstances, including the condition to be treated, the chosen route of administration, the actual compound administered and its relative activity, the age, weight, and response of the individual patient, the severity of the patients symptoms, and the like.

The compound of Formula (I) is preferably administered topically. The daily dose of the compounds may vary depending on the medical condition of the patient, the skin status, and the age of the patient. Compounds of the present invention may be administered in a single daily dose, or the total daily dose may be administered in divided doses of two, three or four times daily. The compound may be applied to the face, scalp, neck, trunk, back, limbs, axillae and/or groin of the human.

The skin surface is preferably dried, and then a compound of Formula (I) is applied to the skin surface of the human at the desired site. The compound can be applied to the face, scalp, neck, trunk, back, limbs, axillae and/or groin of the human. Preferably, the glycopyrrolate compound is applied to the face of the human, in particular the cheeks, neck and forehead, taking care to avoid the eyes, nostrils, and mouth.

Sufficient amounts of the composition are employed to cover (i.e., coat) the entire skin surface with a layer of the compound of Formula (I). If necessary, excess glycopyrrolate compound can be removed from the skin with a wipe or tissue paper.

After application, the compound of Formula (I) penetrates the skin very slowly and has been associated with few side effects[3,4,5]. The compound of Formula (I) is allowed to dry. If desired, cosmetics can be applied over the compound of Formula (I).

Patients susceptible to hot flashes and perspiration associated therewith include, but are not limited to, women undergoing menopause, either natural or surgical; patients taking selective estrogen-receptor modulators (SERMs); patients taking tamoxifen; and male patients undergoing androgen deprivation therapy.

The compounds of the present invention may be administered in a pharmaceutical composition comprising the active compound in combination with a pharmaceutically acceptable carrier adapted for topical administration. Topical pharmaceutical compositions may be in the form of a solution, cream, ointment, mousse, gel, lotion, powder or aerosol formulation adapted for application to the skin. These topical pharmaceutical compositions containing the compounds of the present invention ordinarily include from about 0.05% to 10.0% by weight of the active compound, preferably from about 0.05% to 5.0% by weight of the active compound, more preferably from about 0.5% to 2.5% by weight of the active compound, in admixture with a pharmaceutically acceptable excipient.

Topical preparation containing the active compound can be admixed with a variety of carrier materials or pharmaceutically acceptable excipients well known in the art. When the excipient serves as a diluent, it can be a solid, semi-solid, or liquid, which acts as a vehicle, carrier or medium for the active ingredient. Thus, the compositions can be in die form of powders, suspensions, emulsions, solutions, syrups, alcoholic solutions, ointments, topical cleansers, cleansing creams, skin gels, skin lotions, mousses, roll-ons, aerosol or non-aerosol sprays in cream or gel formulations and soft gelatin capsules.

The compounds of the present invention may be administered in the form of liposome delivery systems, such as small unilamellar vesicles, large unilamellar vesicles and multilamellar vesicles. Liposomes can be formed from a variety of phospholipids, such a cholesterol, stearylamine or phosphatidylcholines.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include alcohols, aloe vera gel, allantoin, glycerin, vitamin A and E oils, mineral oil, PPG2, myristyl propionate lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The glycopyrrolate composition may additionally contain one or more optional additives such as colorants, perfumes, etc. In practice, each of these optional additives should be both miscible and compatible with the glycopyrrolate compound. Compatible additives are those that do not prevent the use of the glycopyrrolate compound in the manner described herein.

Other suitable formulations for use in the present invention can be found in *Remington's Pharmaceutical Sciences*[6].

EXAMPLES

The following preparations and examples are given to enable those skilled in the art to more clearly understand and to practice the present invention. They should not be considered as limiting the scope of the invention, but merely as being illustrative and representative thereof.

Synthetic Example

Glycopyrrolate is readily commercially available. Glycopyrrolate can be made as follows. α-phenylcyclopentaneglycolic acid is esterified by refluxing with methanol in the presence of hydrochloric acid and the resulting ester is transesterified with 1-methyl-3-pyrrolidinol using sodium as a catalyst. The transester is then reacted with methyl bromide to give glycopyrrolate[9,10].

Method of Use

Example 1

The patient is a 56 year old women with a history of hot flashes and perspiration associated with menopause. She complained about profuse facial, scalp and anterior neck sweating that occurred randomly with the hot flashes.

As a treatment, the patient was offered and consented to the application of 0.5% glycopyrrolate topical lotion, which she applied once daily to her forehead and face, sparing her mouth and eyes.

The lotion consisted of 1.5 gm glycopyrrolate; 75 ml ethanol; 2.4 gm hydroxyethylcell; brought to a total volume of 300 ml with water and the pH adjusted to 2–4.5.

This treatment resulted in complete resolution of the perspiration associated with the hot flashes. Daily topical application of the glycopyrrolate roll-on lotion has continued to alleviate her symptoms during the subsequent 6 months that she has used this treatment.

The patient also reported that the application of the glycopyrrolate lotion also alleviated die hot flashes she was experiencing associated with menopause.

Example 2

A 51 year old woman treated with tamoxifen for breast cancer described 8 months of hot flashes and perspiration that awakened her from sleep.

Daily application of 0.5% glycopyrrolate in a "roll on" solution to her face greatly relieved her symptoms and resulted secondarily in improvement in the quality of her sleep.

Example 3

A 48 year old woman treated with tamoxifen for breast cancer described hot flashes and perspiration beginning on her scalp, which interfered with her sleep.

Daily application of 0.5% glycopyrrolate in a "roll on" solution to her scalp and around her hair line greatly relieved her symptoms and resulted in improved sleep.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of die invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method for alleviating menopausal hot flashes in a human, which method comprises:

a) identifying a menopausal human susceptible to hot flashes due to declining estrogen levels; and b) administering to said menopausal human a therapeutically effective amount of a glycopyrrolate analog of Formula (I):

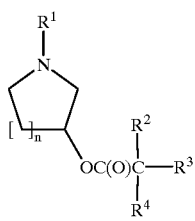

wherein:

n is 1 or 2;

$R^1$ is alkyl or phenylalkyl;

$R^2$ is phenyl which is optionally substituted with alkyl, halo, alkoxy, hydroxy, or acyloxy, or —(alkylene)—$CO_2R^5$ wherein $R^5$ is alkyl, alkenyl, cycloalkyl, or cycloalkenyl;

$R^3$ is cycloalkyl, cycloalkenyl, heteroaryl, phenyl which is optionally substituted with alkyl, halo, alkoxy, hydroxy, or acyloxy;

$R^4$ is hydrogen, hydroxy, or acyl; or an acid addition, alkyl, or benzyl quaternary ammonium salt, individual isomer or a mixture of isomers thereof to a human such that the menopausal hot flashes are substantially reduced.

2. A method for alleviating menopausal hot flashes in a human, which method comprises:

a) identifying a menopausal human susceptible to hot flashes due to declining estrogen levels; and b) administering to said menopausal human a therapeutically effective amount of a glycopyrrolate analog of Formula (II):

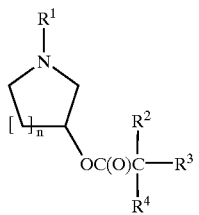

(II)

wherein;

n is 1 or 2;

$R^1$ is alkyl;

$R^2$ is phenyl which is optionally substituted with alkyl, halo, alkoxy, hydroxy, or acyloxy;

$R^3$ is cycloalkyl;

$R^4$ is hydroxy; or an acid addition, alkyl, or benzyl quaternary ammonium salt, individual isomer or a mixture of isomers thereof to a human such that the menopausal hot flashes are substantially reduced.

3. The method according to claim 2 wherein the compound of Formula (II) is where:

n is 1;

$R^1$ is ethyl, propyl, or butyl;

$R^2$ is phenyl which is optionally substituted with methyl, ethyl, propyl, fluoro, chloro, methoxy, ethoxy, hydroxy, or acetyloxy;

$R^3$ is pentyl or hexyl;

$R^4$ is hydroxy.

4. The method according to claim 1 wherein the glycopyrrolate analog is applied to the skin of the human.

5. The method according to claim 2 wherein the glycopyrrolate analog is applied to the skin of the human.

6. The method according to claim 3 wherein the glycopyrrolate analog is applied to the skin of the human.

7. The method according to claim 1, wherein the glycopyrrolate analog is applied to the face and neck of the human.

8. The method according to claim 2, wherein the glycopyrrolate analog is applied to the face and neck of the human.

9. The method according to claim 3, wherein the glycopyrrolate analog is applied to the face and neck of the human.

10. The method according to claim 1, wherein the glycopyrrolate analog is applied to the scalp of the human.

11. The method according to claim 2, wherein the glycopyrrolate analog is applied to the scalp of the human.

12. The method according to claim 3, wherein the glycopyrrolate analog is applied to the scalp of the human.

13. A method for alleviating menopausal hot flashes in a human, which method comprises:

a) identifying a menopausal human susceptible to hot flashes due to declining estrogen levels, and b) administering to said menopausal human a therapeutically effective amount of a pharmaceutical composition comprising a pharmaceutically acceptable excipient and a glycopyrrolate analog of Formula (I):

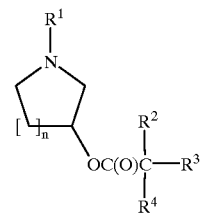

wherein:

n is 1 or 2;

$R^1$ is alkyl or phenylalkyl;

$R^2$ is phenyl which is optionally substituted with alkyl, halo, alkoxy, hydroxy, or acyloxy, or —(alkylene)—$CO_2R^5$ wherein $R^5$ is alkyl, alkenyl, cycloalkyl, or cycloalkenyl;

$R^3$ is cycloalkyl, cycloalkenyl, heteroaryl, phenyl which is optionally substituted with alkyl, halo, alkoxy, hydroxy, or acyloxy;

$R^4$ is hydrogen, hydroxy, or acyl; or an acid addition, alkyl, or benzyl quaternary ammonium salt, individual isomer or a mixture of isomers thereof to a human such that the menopausal hot flashes are substantially reduced.

14. A method for alleviating menopausal hot flashes in a human, which method comprise:

a) identifying a menopausal human susceptible to hot flashes due to declining estrogen levels; and b) administering to said menopausal human a therapeutically effective amount of a pharmaceutical composition comprising a pharmaceutically acceptable excipient and of a glycopyrrolate analog of Formula (II):

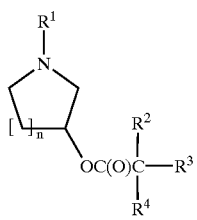 (II)

wherein:
n is 1 or 2;
$R^1$ is alkyl;
$R^2$ is phenyl which is optionally substituted with alkyl, halo, alkoxy, hydroxy, or acyloxy;
$R^3$ is cycloalkyl;
$R^4$ is hydroxy; or
an acid addition, alkyl, or benzyl quaternary ammonium salt, individual isomer or a mixture of isomers thereof to a human such that the menopausal hot flashes are substantially reduced.

15. The method according to claim 14 wherein the compound of Formula (II) is where:
n is 1;
$R^1$ is ethyl, propyl, or butyl;
$R^2$ is phenyl which is optionally substituted with methyl, ethyl, propyl, fluoro, chloro, methoxy, ethoxy, hydroxy, or acetyloxy;
$R^3$ is pentyl or hexyl;
$R^4$ is hydroxy.

16. The method according to claim 13, wherein the concentration of glycopyrrolate analog in the pharmaceutical composition is from 0.05% to 5.0% by weight.

17. The method according to claim 14, wherein the concentration of glycopyrrolate analog in the pharmaceutical composition is from 0.05% to 5.0% by weight.

18. The method according to claim 15, wherein the concentration of glycopyrrolate analog in the pharmaceutical composition is from 0.05% to 5.0% by weight.

* * * * *